US006720432B2

(12) United States Patent
Kozikowski et al.

(10) Patent No.: US 6,720,432 B2
(45) Date of Patent: Apr. 13, 2004

(54) SYNTHESIS OF EPECATECHIN-4α, 8-EPICATECHIN DIMERS AND DERIVATIVES THEREOF

(75) Inventors: Alan P. Kozikowski, Princeton, NJ (US); Leo J. Romanczyk Jr., Hackettstown, NJ (US); Werner Tückmantel, Washington, DC (US)

(73) Assignee: Mars Incorporated, McLean, VA (US)

( * ) Notice: Subject to any disclaimer, the term of this patent is extended or adjusted under 35 U.S.C. 154(b) by 0 days.

(21) Appl. No.: 10/214,830

(22) Filed: Aug. 8, 2002

(65) Prior Publication Data

US 2003/0100775 A1 May 29, 2003

Related U.S. Application Data

(62) Division of application No. 09/655,360, filed on Sep. 5, 2001, now Pat. No. 6,476,241.

(51) Int. Cl.$^7$ ............................................. C07D 315/00
(52) U.S. Cl. ....................................................... 549/415
(58) Field of Search ......................................... 549/415

(56) References Cited

U.S. PATENT DOCUMENTS 5,554,645 A    9/1996 Romanczyk, Jr. et al. .. 514/453

FOREIGN PATENT DOCUMENTS

| DE | 1518003 | 1/1969 |
| EP | 0 039 844 | 11/1981 |
| EP | 1 026 164 A1 | 8/2000 |
| WO | WO 90/13304 | 11/1990 |
| WO | WO 99/19319 | 4/1999 |

OTHER PUBLICATIONS

Ishimaru et al., Phytochemistry, (1987), vol. 26, No. 4, pp. 1160–1170.*
Delcour et al., L. Chem. Soc., Perk. Transl., (1985), vol. 4, pp. 669–676.*
Beckett, "Industrial Chocolate Manufacture and Use", *Blackie*, 1988, 109–121.
Balas et al., "2D NMR Structure Elucidation of Proanthocyanidins: the Special Case of the Catechin–(4α–8)–catechin–(4α–8)–catechin Trimer", *Magnetic Resonance in Chemistry*, 1995, 33, N2, p. 85–94.
Botha et al., "Synthesis of Condensed Tannins. Part 5. The First Angular [4,6:4,8]–Triflavanoids and Their Natural Counterparts", *Journal of the Chemical Society*, 1982, 527–533.
Delcour et al., "Synthesis of Condensed Tannis. Part 9.+ The Condensation Sequence of Leucocyanidin with (+)–Catechin and with the Resultant Procyanidins", *J. Chem. Soc. Perkin Trans.*,1983, 1711–1717.

Ferreira et al., "Diversity of Structure and Function in Oligomeric Flavanoids", *Tetrahedron Report No. 308*, 1992, 48(10), p. 1743–1803.
Foo, et al., "Condensed Tannins: Synthesis of the First 'Branched' Procyanidin Trimer", *J. Chem., Soc., Chem. Commun.*, 1984, 85–86.
Kawamoto et al., "Synthesis of Condensed Tannin Derivatives Regiospecifically Linked through a Single Interflavanoid–Linkage and Their Protein–Precipitating Capacities", *Mokuzai Gakkaishi*, 1991 37(8), p 741–747.
Keogh et al., "A new synthesis of flavans", *Chem. Ind.*, 1961, 3398.
Kiehlmann, et al., "Iodination and deuteration of catechin derivatives", *Can. J. Chem.*, 1988, 66, p. 2431–2439.
Kim et al., "(−)–Epicatechin Content in Fermented and Unfermented Cocoa Beans",*Journal of Food Science*, 1984, 49(4), 1090–1092.
Pierre et al., "Deuterium Labeled Procyanidin Syntheses", *Tetrahedron Letters*, 1997, 38(32), p. 5639–5642.
Saito, Akiko et al., "Synthetic Studies of Proanthocyanidins. Highly Stereoselective Synthesis of the Catechin Dimer, Procyanidin–B3", *Biosci. Biotechnol. Biochem.*, 66(8), 1764–1767, 2002.
Weinges et al., "Synthese des Octamethyl–diacetyl–procyanidins B3", *Chem. Ber.*, 1970, 103, 2344–2344.
Kozikowski, et al., "Studies in Polyphenol Chemistry and Bioactivity", J. Org. Chem. 2001, 66, 1287–1296.
Tückmantel "Studies in Polyphenol Chemistry and Bioactivity", J. Am. Chem. Soc. 1999, 121, 12073–12081.
Kozikowski et al. "Studies in Polyphenol Chemistry and Bioactivity", J. Org. Chem. 2000, 66, 5371–5381.
Delcour, J. et al., "Direct Synthesis of the Barley Proanthocyanidins Prodelphinidin B3, Prodelphinidin C2 and Two Trimeric Proanthocyanidins with a Mixed Prodelphinidin–Procyanidin Stereochemistry", *J. Inst. Brew*, 1986, vol. 92, pp. 244–249.

* cited by examiner

*Primary Examiner*—Taofiq Solola
(74) *Attorney, Agent, or Firm*—Margaret B. Kelley; Clifford Chance, LLP

(57) ABSTRACT

Oligomeric procyanidins containing 4α-linked epicatechin units are rare in nature and have hitherto not been accessible through stereoselective synthesis. Provided herein is the preparation of the prototypical dimer, epicatechin-4α,8-epicatechin, by reaction of the protected 4-ketones with aryllithium reagents derived by halogen/metal exchange from the aryl bromides. Removal of the 4-hydroxyl group from the resulting tertiary benzylic alcohols is effected by tri-n-butyltin hydride and trifluoroacetic acid in a completely stereoselective manner, resulting in hydride delivery exclusively from the β face.

18 Claims, No Drawings

SYNTHESIS OF EPECATECHIN-4α, 8-EPICATECHIN DIMERS AND DERIVATIVES THEREOF

This application is a divsional of prior application Ser. No. 09/655,360 filed Sep. 5, 2001, now U.S. Pat. No. 6,476,241.

FIELD OF THE INVENTION

This invention, in general, relates to polyphenolic products, particularly proanthocyanidins. The invention further relates to synthetic processes for preparing polyphenolic natural products and other related compounds.

BACKGROUND OF THE INVENTION

Proanthocyanidins (nonhydrolyzable tannins) are a group of polyphenolic natural products, of current interest because of their numerous biological activities, their widespread occurrence in foodstuffs, and their resulting relevance for human health.

Proanthocyanidins are dimeric or oligomeric flavanoids which have one or several hydroxyl groups on their aromatic rings and often an additional hydroxyl group in the 3 position. Eleven different hydroxylation patterns of the A and B rings have been found in nature. Representative proanthocyanidins include:

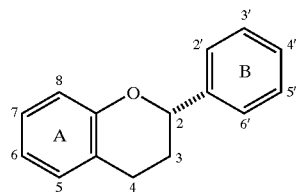

| Class | Monomer | Substitution Pattern | | | | | | |
|---|---|---|---|---|---|---|---|---|
| | | 3 | 5 | 7 | 8 | 3' | 4' | 5' |
| Proapigeninidin | Apigeniflavan | H | OH | OH | H | H | OH | H |
| Proluteolinidin | Luteoliflavan | H | OH | OH | H | OH | OH | H |
| Protricetinidin | Tricetiflavan | H | OH | OH | H | OH | OH | OH |
| Propelargonidin | Afzelechin | OH | OH | OH | H | H | OH | H |
| Procyanidin | Catechin | OH | OH | OH | H | OH | OH | H |
| Prodelphinidin | Gallocatechin | OH | OH | OH | H | OH | OH | OH |
| Proguibourtinidin | Guibourtinidol | OH | H | OH | H | H | OH | H |
| Profisetinidin | Fisetinidol | OH | H | OH | H | OH | OH | H |
| Prorobinetinidin | Robinetinidol | OH | H | OH | H | OH | OH | OH |
| Proteracacinidin | Oritin | OH | H | OH | OH | H | OH | H |
| Promelacacinidin | Prosopin | OH | H | OH | OH | OH | OH | H |

The stereochemistry of the substituents on a polyphenol monomeric unit of a proanthocyanidin may be described in terms of their relative stereochemistry, "alpha/beta" or "cis/trans". The term "alpha" (α) indicates that the substituent is oriented below the plane of the flavan ring, whereas, "beta" (β) indicates that the substituent is oriented above the plane of the ring. The term "cis" indicates that two substituents are oriented on the same face of the ring, whereas "trans" indicates that two substituents are oriented on opposite faces of the ring.

The isolation of pure proanthocyanidins from natural sources becomes increasingly difficult with increasing degree of oligomerization. Degradation by thiolysis permits identification of the underlying monomeric units but the tasks of elucidating the position and stereochemistry of the interflavan linkages is nontrivial. Both of these factors have resulted in few defined oligomers above the tetramer being described in the prior art. Proanthocyanidins and their parent monomers also occur naturally in the form of a variety of derivatives, for example, glycosides or esters with hydroxylated aromatic carboxylic acids, such as gallic or hexahydroxydiphenic acid.

Among the proanthocyanidins, two subtypes, the procyanidins (5,7,3',4'-hydroxylation) and prodelphinidins (5,7,3',4',5'-hydroxylation), are widespread in human foodstuffs, e.g., cocoa. Cocoa procyanidins consist predominantly of epicatechin (the C-3 epimer of catechin) building blocks. Oligomers up to the size of the decamer have been identified. From the pentamer on, these oligomers exhibit growth inhibitory activity against various cancer cell lines. (Romanczk, L. J. Jr.; Hammerstone, J. F., Jr.; Buck, M. M. U.S. Pat. No. 5,554,645, Sep. 10, 1996.) Flavan-3-ols are biosynthetically derived from (2S)-phenylalanine via flavan-3,4-diols. These latter intermediates readily form a highly stabilized carbenium ion (or quinone methide) in position C-4 which attacks the A ring of a flavan-3-ol in what is essentially a Friedel-Crafts alkylation process, forming an interflavan bond. This process can be repeated once or several times, resulting in chain-type oligomers which together with the dimers are known as non-hydrolyzable tannins, condensed tannins, or proanthocyanidins. As one skilled in the art will realize, the structural complexity of these compounds rapidly increases with their chain length as a consequence of different hydroxylation patterns and C-3 stereochemistry in the monomer unit and different regio- and stereochemistries of the interflavan linkages, as well as additional structural modifications. In addition, chain branching may occur by alkylation of a monomer unit in both its 6- and 8-positions.

To prove definitively the structures assigned to the compounds purified from cocoa, comparisons must be made to epicatechin dimers and oligomers of defined structure prepared synthetically. Synthetic monomers, dimers and oligomers are useful to develop structure-activity relationships in various in vitro and ultimately in vivo models of anticancer activity.

The synthetic challenge posed by procyanidins is related to the difficulty in controlling the interflavan regio- and stereochemistry, as well as the sensitivity of the nonprotected compounds to acids, bases, and oxidizing agents. The condensation between flavan-3-ols and 4-substituted, electrophilic flavans has traditionally been performed without the use of phenol protecting groups in a mildly acidic medium or recently, with $AgBF_4$ for benzylthio as the 4-substituent. The products are mixtures of regio- and sometimes stereoisomers, as well as higher oligomers despite the application of an excess of the nucleophilic building block. They have usually been separated by gel chromatography on Sephadex LH-20, a process that requires a considerable investment of time to develop for each particular separation task because of the unavailability of fast analytical tools such as HPLC columns or thin layer plates for this adsorbent. In addition, optically pure, nonprotected 4-substituted catechins and epicatechins are not readily available, being prepared by reduction of the expensive natural product, (+)-taxifolin (the 4-ketone) or by in situ degradation or thiolytic degradation of natural proanthocyanidin oligomic fractions for which commercial sources are difficult to identify or nonexistant.

It is therefore not surprising that prior art syntheses have used protected oligomeric procyanidins as building blocks. As an additional incentive, protection of the phenolic but not of the alcoholic hydroxyls would permit the regioselective elaboration of derivatives such as 3-esters and -glycosides, as has been done in the case of catechin using acetyl protecting groups. An interesting approach has been reported in which the 8-bromo derivative of 3-O-benzyl-5,7,3',4'-tetra-O-methylcatechin was subjected to halogenlithium exchange and reacted with an O-methylated 4-ketone, thus ensuring complete regiocontrol. However, the methyl O-blocking groups cannot be removed to obtain the free dimer. The remaining published work has made use of the above-described electrophilic substitution process with inclusion of phenol protecting groups on one or both of the reaction partners.

Our own previous work directed toward the synthesis of defined epicatechin oligomers used the $TiCl_4$-mediated alkylation of 5,7,3',4'-tetra-O-benzyl-(−)-epicatechin with 5,7,3',4'-tetra-O-benzyl-4-(2-hydroxyethoxy)epicatechin. Besides higher oligomers, whose yields rapidly decrease with increased molecular mass, a single dimeric product having beta stereochemistry of the interflavan bond (a procyanidin $B_2$ derivative) was obtained.

Until quite recently, the analytical methods employed for the assignment of interflavan bond regio- and stereochemistry in these compounds were not validated by an independent confirmation of the structure of any dimeric proanthocyanidin. The application of X-ray crystallography has been prevented by the poor crystallizability of proanthocyanidins and their derivatives. Assignments of stereochemistry on the basis of $^1H$ NMR coupling constants and circular dichroism disregard the basic fact that the C rings are conformationally flexible. From a conservative point of view, postulates of specific conformations of flexible molecules, regardless of their source (intuitive or computational), cannot be considered a prudent approach to structure elucidation.

Advances in synthetic methodology, which have taken place after the isolation of numerous proanthocyanidins from natural sources, have now enabled one to obtain a definitive proof of the previously conjectured 4β stereochemistry in procyanidin $B_2$. A differentially protected epicatechin dimer, correlated with procyanidin $B_2$ through a common derivative, was subjected to a series of defunctionalization steps and finally degraded to (R)-(−)-2,4-diphenylbutyric acid, isolated as its benzhydryl ester. The sole remaining asymmetric center of this degradation product is directly derived from C-4 of the "top" epicatechin moiety in procyanidin $B_2$, and the sign of the optical rotation of the degradation product, the absolute configuration of which was established by X-ray crystallography, thus revealed the absolute configuration at C-4.

Those skilled in the art will recognize the importance of having an authentic sample of the opposite stereoisomer, now recognizable by default as epicatechin-4α,8-epicatechin for comparison. Literature reports of proanthocyanidins for which simultaneously a 2,3-cis and a 3,4-cis relationship of their C-ring substituents has been postulated are scarce, and epicatechin-4α,8-epicatechin has not been isolated from natural sources. In fact no stereoselective synthesis of any procyanidin containing a 4α-linked unit has been reported to date.

It is a plausible assumption that, in the course of the formation of the 4β,8-dimer, the 2-aryl group and the 3-oxygen cooperate in directing the approach of the flavan nucleophile to the presumed carbocationic intermediate towards its β-face. Therefore, accessibility of the 4α-stereoisomer by merely modifying the reaction conditions or attaching protecting groups to one or both of the 3-hydroxyl groups was deemed unlikely. Hence, there is a need for a new synthetic process for the preparation of epicatechins substituted at the 4α position. The instant disclosure is addressed to that unmet need.

SUMMARY OF THE INVENTION

The process of the present invention allows one to prepare unprotected epicatechin derivatives substituted at the 4α position, preferably with an aromatic radical. In one preferred embodiment, the dimer epicatechin-4α,8-epicatechin is prepared. One advantage of the present invention is the formation of nonpolar intermediates which can be more readily separated at each step than polar, more sensitive final intermediates.

A crucial step in the present process is a transformation wherein a C-4-carbocation which has an aromatic unit already in place, is attacked by a hydride nucleophile from its β-face, which forces the 4-aryl group to occupy the α-face. The carbocation would be conveniently generated from a tertiary alcohol which, in turn, is accessible from an aryl organometallic reagent and a protected 4-keto-epicatechin.

This invention is directed to a process for preparing 4α-aryl substituted epicatechins. The process comprises the steps of:

(A) forming a suitably protected epicatechin by protecting the C-3 hydroxyl group of 5,7,3',4'-tetra-O-benzylepicatechin with a protecting group to produce a compound having the formula:

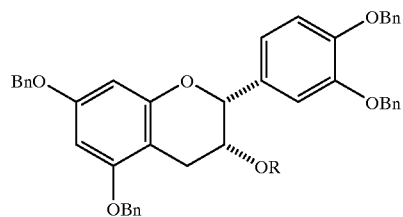

where Bn is a benzyl group and R is a hydroxyl protecting group.

(B) oxidizing the 4-position of the protected epicatechin to produce a protected flavan-4-one having the formula:

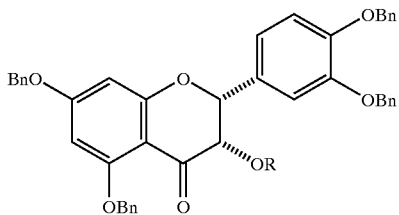

(C) contacting the flavan-4-one with a nucleophilic aryl organometallic reagent to produce a compound of formula:

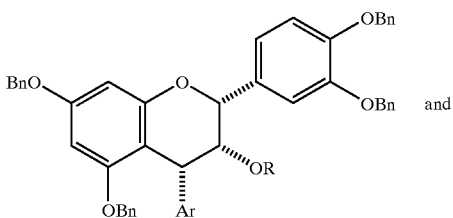

(D) deoxygenating the C-4 position stereoselectively to produce a compound of formula:

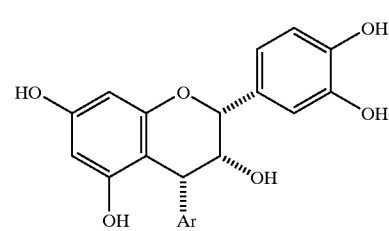

and (E) optionally deprotecting the C-3 hydroxyl group and then further optionally acylating the C-3 hydroxyl group with a suitable acylating agent and subsequently removing the benzyl groups; or (A) optionally deprotecting the C-3 hydroxyl group and removing the benzyl groups to produce a free 4α-aryl-epicatechin having the formula:

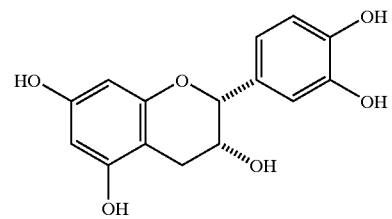

Also provided is a process for the preparation of other derivatives of the 4α-arylepicatechin by acylating the phenolic groups after removal of the benzyl groups.

In one aspect, the invention relates to a process for the preparation of epicatechin-epicatechin dimers where the nucleophilic aryl organometallic reagent is derived from a protected 8-bromoepicatechin or derivative thereof.

PROPOSED EMBODIMENTS

As used herein, the term epicatechin (an epimer of catechin) refers to a compound of formula:

5,7,3',4'-Tetra-O-benzylepicatechin refers to an epicatechin where the proton of each phenolic hydroxyl group is replaced by a benzyl group. Those skilled in the art of organic synthesis will recognize that there may be many methods of preparing tetra-O-benzylepicatechin. One particularly useful method of obtaining such a compound has been described by Tückmantel et al. *J. Am. Chem. Soc.* 1999, 121, 12073–12081.

As used herein, "aryl" means an aromatic hydrocarbon compound or heterocycle. The aryl group may be phenyl or substituted phenyl, wherein substituents are selected from the group consisting of halo, aryl, $C_1$–$C_6$-alkyl, $C_1$–$C_6$ haloalkyl, $C_1$–$C_6$ alkoxy, $C_3$–$C_8$ cycloalkyl, and $C_3$–$C_8$ cycloalkoxy provided that they are compatible with the formation of a nucleophilic organometallic reagent. The aryl group may be embedded in a ring-system of other aromatic or saturated hydrocarbon rings or heterocycles.

An important transformation in the present process is the protection of the hydroxyl group at the C-3 position of 5,7,3',4'-tetra-O-benzylepicatechin. In one embodiment the protection involves alkylation with a benzyl halide, such as benzyl bromide to obtain a fully protected epicatechin. Typically, the reaction is conducted in the presence of a base, preferably a strong base such as an alkali metal hydride, dialkylamide, bis(trialkylsilyl)amide or hydroxide, more preferably an alkali metal hydride such as sodium hydride. The reaction is typically carried out in an a polar organic solvent. Those skilled in the art will be able to select a solvent that is compatible with a particular base. A preferred solvent may be acetonitrile, tetrahydrofuran (THF), N,N-dimethylformamide, a sulfoxide such as dimethylsulfoxide, orN-methylpyrrolidinone. A more preferred solvent is an amide such as N,N-dimethylformamide. A typical reaction temperature is between about 0° C. and the reflux temperature of the solvent, preferably a temperature between 15° C. and about 40° C., more preferably about 23° C. After addition of all the reagents, a reaction typically is stirred for a period between 15 minutes and 24 hours, preferably between 30 minutes and 1 hour.

In another embodiment, the protecting group used to protect the hydroxyl group at the C-3 position of 5,7,3',4'-tetra-O-benzylepicatechin is orthogonal to a benzyl group. Typically the reaction involves O-silylation of the C-3 hydroxyl group to obtain a silyl ether. The silylating agent may be a silyl chloride. When the alkyl substituents on the silicon are tert-butyldimethyl, the silylating agent is tert-butyldimethylsilyl chloride, and the reaction is carried out in the presence of a mild base such as imidazole, or triethylamine with 4-(dimethylamino)pyridine. The reaction is carried out in an inert polar organic solvent, preferably N,N-dimethylformamide, dichloromethane, or THF. Typically the O-silylation reaction occurs at temperature between 0° C. and about 40° C., preferably at between about 15° C. and about 30° C., more preferably about 23° C., for a period between about 1 and about 24 hours, preferably for a period between about 6 and 12 hours, more preferably for about 12 hours. Those skilled in the art will recognize other methods of silylating hydroxyl groups are suitable. The silylating agent may be a silyl trifluoromethanesulfonate in which case the preferred base is pyridine or 2,6-lutidine and the solvent is dichloromethane or chloroform.

Those skilled in the art will recognize that the C-3 hydroxyl of 5,7,3',4'-tetra-O-benzyl-8-bromoepicatechin or 5,7,3',4'-tetra-O-benzyl-8-bromoepicatechin can be protected in a similar manner.

Another important step in the present process is the oxidation of the protected epicatechin. The oxidation can be carried out using any suitable oxidant. Typically, the oxidation is carried out in two steps. The first step involves the transformation of the C-4 methylene to a secondary alcohol to provide a protected 4-hydroxyepicatechin, presumably having 4β stereochemistry. The reaction is typically carried out by contacting a protected epicatechin with an oxidizing agent, preferably a reagent that has been employed to oxidize O-alkylated catechins and epicatechins, such as lead tetraacetate, or 2,3-dichloro-5,6-dicyano-p-benzoquinone (DDQ). More preferably an electron poor quinone type oxidizing agent such as DDQ or a variation thereof is used. The reaction is carried out in an organic solvent, preferably a dialkyl ether, where the alkyl groups have between 1 and 4 carbon atoms, a cyclic ether such as tetrahydrofuran, or a chlorinated solvent such as dichloromethane or chloroform. When DDQ is the oxidizing agent water is present in the solvent. The reaction is typically carried out at a temperature between 0° C. and the reflux temperature of the solvent, preferably at a temperature about 15° C. to about 30° C., more preferably at about 23° C., and for a period of time between about 1 and about 24 hours, preferably about 6 to about 12 hours, more preferably about 12 hours.

The second step is a further oxidation involving the conversion of the protected 4-hydroxyepicatechin to a protected flavan-4-one. The reaction is carried out in the presence of an oxidizing agent, preferably an oxidizing agent formed by combining N-methylmorpholine-N-oxide and tetrapropylammonium perruthenate, and in the presence of a non-reactive drying agent, preferably molecular sieves. This oxidation technique is described by Ley et al. in *J. Chem. Soc., Chem. Commun.* 1987, 1625. Typically such a reaction is carried out in an organic solvent, preferably a chlorinated alkane such as dichloromethane, at a temperature of between 0° C. and the reflux temperature of the solvent, preferably between the temperature of 15° C. and 30° C., more preferably at a temperature of 23° C., and for a period of between 1 and 24 hours, preferably for a period of between 6 and 12 hours, more preferably for a period of 12 hours.

A further transformation in the present process involves the reaction of the protected flavan-4-one with a nucleophilic aryl organometallic reagent to produce a protected 4-aryl-4-hydroxyepicatechin. Typically the reaction is carried out by first forming a nucelophilic aryl organometallic reagent in situ by combining an aryl halide preferably an aryl bromide, with an alkyllithium, preferably with tert-butyllithium, in an anhydrous ether solvent, preferably tetrahydrofuran, under an inert atmosphere, at a temperature of between about −100° C. and 0° C., for a period of between about 1 and about 24 hours, and then contacting the formed nucleophilic aryl organometallic reagent with the protected flavan-4-one, also in an anhydrous ether solvent, preferably tetrahydrofuran, in an inert atmosphere, at a temperature of between −100° C. and 0° C., for a period of between about 1 and about 24 hours. Those skilled in the art will recognize that other organometallic reagents such as Grignard reagents may be employed in present invention.

Those skilled in the art will also recognize that certain nucleophilic aryl organometallic reagents may be formed from materials other than aryl halides. In particular nucleophilic aryl organometallic reagents may be prepared by processes known in the art as ortho metallation and transmetallation.

One particular embodiment of the present invention provides for the reaction of 2,4,6-trimethoxyphenyllithium with a protected flavan-4-one. Another particular embodiment of the instant invention contemplates the treatment of protected 8-bromoepicatechin or protected 8-bromoepicatechin or protected 8-bromocatechin with tert-butyllithium to form the nucleophilic organometallic reagent of the invention. A typical protected 8-bromo-epicatechin is 5,7,3',4'-tetra-O-benzyl-8-bromo-3-O-(tert-butyldimethylsilyl)epicatechin, which is treated with an alkyllithium, preferably tert-butyllithium, in an anhydrous ether solvent, preferably tetrahydrofuran, under an inert atmosphere, at a temperature of between about −100° C. and 0° C., for a period of between about 1 and about 24 hours, and then contacting the resulting aryllithium with a protected flavan-4-one, also in an anhydrous ether solvent, preferably tetrahydrofuran, in an inert atmosphere, at a temperature of between −100° C. and 0° C., for a period of between about 1 and about 24 hours.

The process of the present invention provides for the deoxygenation of the protected 4-aryl-4-hydroxyepicatechin at C-4 to give a protected 4α-arylepicatechin as a single stereoisomer. The deoxygenation is carried out in the presence of a reducing agent, preferably a reducing agent formed by combining a trialkylsilane in which each alkyl group contains between 1 and 4 carbon atoms, with an organic acid, in an inert organic solvent, preferably a chlorinated alkane such as dichloromethane, at a temperature between 0° C. and the reflux temperature for a period between about 5 minutes and about 24 hours. More preferably the reaction is carried out in the presence of a reducing agent formed by combining a trialkyltin hydride in which each alkyl portion contains between 1 and 6 carbon atoms with a perfluorocarboxylic acid, in an inert organic solvent, preferably a chlorinated alkane such as dichloromethane, at a temperature between 0° C. and the reflux temperature for a period of between about 5 minutes and about 24 hours.

The invention further provides for a protected 4-aryl-5,7,3',4'-tetra-O-benzylepicatechin to be deprotected at the C-3 hydroxyl group, or when the 4-aryl substituent is itself an epicatechin, at both C-3 hydroxyl groups. In the embodiment wherein the C-3 hydroxyl group is protected by a silyl group, the deprotection reaction is carried out with fluoride, typically with aqueous hydrofluoric acid in acetonitrile. As those skilled in the art will recognize the C-3 hydroxyl group(s) may be further derivatized after being deprotected. Typically the derivatization will involve acylating the C-3 hydroxyl group with an acylating agent such as an activated acid or acid chloride. A preferred acylating agent is one formed by activating tri-O-benzylgallic acid as an acid chloride. Those skilled in the art will recognize that acids may be activated in a variety of ways to from suitable acylating agents.

Another important step of the process involves the removal of benzyl groups. Benzyl groups may be removed from protected aromatic hydroxyl groups (i.e. phenols) and protected aliphatic hydroxyl groups by hydrogenolysis. Typically, the hydrogenolysis reaction is carried out in an atmosphere of hydrogen gas either at standard temperature and pressure or preferably at elevated pressure of about 1–5 bar, more preferably at about 3.5–5 bar in a suitable organic solvent such as methanol, ethanol, ethyl acetate or a mixture thereof Typically a metal catalyst is used to facilitate the removal of benzyl groups. Preferred catalysts are Pd, Pt, or Ni adsorbed onto a solid support, a more preferred catalyst is palladium hydroxide adsorbed on carbon. However, those skilled in the art will recognize that a variety of other catalyst can be employed to facilitate the removal of benzyl groups. In one embodiment, the removal of the benzyl groups produces a free 4-arylepicatechin which may be isolated and purified. Alternatively, the crude hydrogenolysis product can be directly converted into its acetate derivative, by reacting the crude product with acetic anhydride and a base. In a more preferred embodiment where the 4-aryl substituent is epicatechin, the hydrogenolysis produces a free epicatechin-4α,8-epicatechin and acetylation produces the decaacetate derivative. As these acetate derivatives are shown to be different from their C-4 epimers by $^1$H NMR spectroscopy, and as the 4,8-position of their interflavan linkage is a necessary consequence of the structure of the starting material, the free epicatechin dimer produced by this process is unequivocally identified as the hitherto unknown epicatechin-4α,8-epicatechin.

In another embodiment, benzyl groups are removed after the C-3 hydroxyl groups have been acylated to produce the free 4-arylepicatechin derivatized at C-3.

The instant invention also provides for the removal of benzyl groups that are introduced as a component of the acylating agent. In a preferred embodiment wherein at least one C-3 hydroxyl group is acylated by an activated derivative of tri-O-benzylgallic acid, the benzyl groups on the gallate hydroxyl groups can be removed in a single step together with the removal of the benzyl groups from the epicatechin core.

The invention is further described by the following non-limiting examples.

EXAMPLES

General Procedures. Pearlman's catalyst (20% palladium hydroxide on carbon) was obtained from Aldrich and contained ≦50% water. $^1$H and $^{13}$C NMR spectra were acquired at nominal frequencies of 300 and 75 MHz, respectively. $^1$H NMR spectra are referenced to internal TMS, $^{13}$C NMR spectra to internal TMS if so marked, otherwise to the CDCl$_3$ signal (δ77.00). Combustion analyses: Micro-Analysis, Inc. (Wilmington, Del.). Column chromatography (cc): Merck silica gel 60 (No. 7734-7), particle size 63–200 μm. Thin layer chromatography: Merck silica gel 60 F$_{254}$ (No. 7734-7), layer thickness 250 μm; visualization with alkaline potassium permanganate solution.

Example 1
Preparation of 3,5,7,3',4'-penta-O-benzylepicatechin.

To a suspension of 180 mg (4.5 mmol) of sodium hydride (60% in oil) in 10 mL of dry N,N-dimethylformamide (Tückmantel et al. *J. Am. Chem. Soc.* 1999, 121, 12073–12081) was added at room temperature a solution of 2.60 g (4.00 mmol) of 5,7,3',4'-tetra-O-benzylepicatechin in 10 mL of dry N,N-dimethylformamide. After 1 hour, 0.56 mL (4.7 mmol) of benzyl bromide was added. The mixture was stirred overnight, poured into ice water, and extracted with 3 times 50 mL of dichloromethane. The combined organic phases were washed with water and brine, dried over magnesium sulfate, and evaporated. The residue was purified by column chromatography (dichloromethane/ethyl acetate/hexane 1:1:6) to give 2.20 g (74%) of the product as a colorless, amorphous solid: $[\alpha]_D$–30.7°, $[\alpha]_{546}$–37.2° (c 6 gL$^{-1}$, ethyl acetate); $^1$H NMR (CDCl$_3$) δ7.48–7.25 (m, 20H), 7.19 (s, 1H), 7.17–7.12 (m, 3H), 7.04–6.97 (m, 2H), 6.91 (narrow ABq, 2H), 6.27, 6.25 (ABq, 2H, J=2 Hz), 5.17 (s, 2H), 5.05 (s, 2H), 5.00 (s, 2H), 4.98 (s, 2H), 4.94 (s, 1H), 4.44, 4.30 (ABq, 2H, J=12.5 Hz), 3.91 (narrow m, 1H), 2.99, 2.77 (ABq, 2H, J=17 Hz, both parts d with J=2.5 and 4 Hz, resp.); $^{13}$C NMR (CDCl$_3$) δ158.59, 157.95, 155.56, 148.75, 148.33, 138.07, 137.37, 137.28, 137.07, 136.94, 132.20, 128.49, 128.45, 128.38, 128.32, 128.03, 127.87, 127.78, 127.67, 127.61, 127.57, 127.49, 127.32, 127.23, 127.17, 119.75, 114.69, 113.80, 101.45, 94.73, 93.73, 78.02, 72.55, 71.31, 71.14, 71.02, 70.03, 69.86, 24.47; IR (film) 1617, 1592, 1145, 1116, 735, 696 cm$^{-1}$. Anal. Calcd. for C$_{50}$H$_{44}$O$_6$: C, 81.06; H, 5.99. Found: C, 81.19; H, 5.76.

Example 2
Preparation of 3,5,7,3',4'-penta-O-benzyl-4-hydroxyepicatechin.

To a solution of 2.20 g (3.38 mmol) of 3,5,7,3',4'-penta-O-benzylepicatechin in 20 mL of tetrahydrofuran and 0.16 mL (8.9 mmol) of water was added at room temperature 2.00 g (7.4 mmol) of 2,3-dichloro-5,6-dicyano-p-benzoquinone. The mixture was stirred overnight, then 0.91 g (7.4 mmol) of 4-(dimethylamino)pyridine was added, stirring was continued for 5 min, and 20 g of silica gel was added. After evaporation, the residue was filtered over silica gel (ethyl acetate/hexane 1:4, then dichloromethane/ethyl acetate/hexane 1:1:4) to give 1.05 g (47%) of the product as a white foam: $[\alpha]_D$+6.6°, $[\alpha]_{546}$+7.2° (c 10 gL$^{-1}$, ethyl acetate); $^1$H NMR (CDCl$_3$) δ7.50–7.28 (m, 20H), 7.20–7.11 (m, 4H), 7.04–6.92 (m, 4H), 6.30 (narrow m, 2H), 5.20 (s, 2H), 5.09 (narrow ABq, 2H), 5.06 (s, 2H), 5.03 (s, 1H), 5.01 (s, 2H), 4.95 (narrow m, 1H), 4.39, 4.25 (ABq, 2H, J=12 Hz), 3.70 (narrow m, 1H), 2.41 (d, 1H, J=2 Hz); $^{13}$C NMR (CDCl$_3$) δ160.32, 159.00, 156.09, 148.88, 148.39, 137.61, 137.38, 137.26, 136.64, 136.48, 131.58, 128.70, 128.59, 128.43, 128.38, 128.14, 128.06, 127.78, 127.63, 127.68, 127.54, 127.49, 127.35, 127.31, 127.28, 119.88, 114.82, 113.61, 104.77, 94.79, 94.06, 77.07, 74.83, 72.49, 71.34, 70.98, 70.20, 70.10, 61.10; IR (film) 1616, 1592, 1152, 1120, 736, 696 cm$^{-1}$. Anal. Calcd. for C$_{50}$H$_{44}$O$_7$: C, 79.34; H, 5.86. Found: C, 79.91; H, 5.60.

Example 3
Preparation of (2R,3S)-3,5,7,3',4'-pentakis (benzyloxy) flavan-4-one To a solution of 1.00 g (1.32 mmol) of 3,5,7,3',4'-penta-O-benzyl-4-hydroxyepicatechin in 8 mL of dry dichloromethane was added at room temperature 300 mg of 4 Å molecular sieves, 180 mg (1.54 mmol) of N-methylmorpholine-N-oxide, and 58 mg (165 μmol) of tetrapropylammonium perruthenate. The reaction mixture was stirred overnight and evaporated, and the residue was purified by column chromatography (ethyl acetate/dichloromethane/hexane 1:1:10) to give 0.66 g (66%) of the ketone as a white foam: $\alpha_D$–47.9°, $\alpha_{546}$–58.5° (c 10 gL$^{-1}$, ethyl acetate); $^1$H NMR (CDCl$_3$) δ7.67–7.38 (m, 20H), 7.27 (s, 1H), 7.24–7.22 (m, 3H), 7.12–7.10 (m, 2H), 7.02 (m, 2H), 6.33 (d, 1H, J=2.1 Hz), 6.29 (d, 1H, J=2.1 Hz), 5.34 (d, 1H, J=1.2 Hz), 5.26 (d, 2H), 5.24 (s, 2H), 5.14 (s, 2H), 5.09 (s, 2H), 4.78 (d, 1H, J=12.0 Hz), 4.50 (d, 1H, J=12.0 Hz), 3.85 (d, 1H, J=1.8 Hz); $^{13}$C NMR (CDCl$_3$) δ187.59, 165.12, 164.53, 161.71, 149.06, 148.96, 137.37, 137.32, 137.30, 136.56, 135.89, 129.25, 128.85, 128.71, 128.63, 128.57, 128.49, 128.219, 128.154, 127.94, 127.91, 127.78, 127.72, 127.50, 127.37, 126.30, 120.29, 114.64, 114.08, 104.70, 95.47, 94.76, 80.96, 79.26, 72.30, 71.34, 71.22, 70.44; IR (film) 3031, 2870, 1673, 1606, 1572, 1512, 1454, 1269, 1165, 1120, 1025, 736, 696 cm$^{-1}$. Anal. Calcd. for C$_{50}$H$_{42}$O$_7$: C, 79.56; H, 5.61. Found: C, 79.99; H, 5.31.

Example 4

Preparation of 3,5,7,3',4'-penta-O-benzyl-4-hydroxy-4-(2,4,6-trimethoxyphenyl)epicatechin To a solution of 32 mg (130 µmol) of 1-bromo-2,4,6-trimethoxybenzene in 1 mL of dry tetrahydrofuran was added at −78° C. 85 µL (145 µmol) of tert-butyllithium (1.7 M in pentane). After 1 hour at −78° C., a solution of 50 mg (66 µmol) of (2R,3S)-3,5,7,3',4'-pentakis(benzyloxy)flavan-4-one in 1 mL of dry tetrahydrofuran was added. After another 3 hours at −78° C., 2 mL of aq. ammonium chloride solution was added, and the product was extracted into three times 10 mL of dichloromethane. The combined organic phases were dried over magnesium sulfate and evaporated, and the residue was purified by column chromatography (ethyl acetate/hexane 1:4) to give 25 mg (45%) of the product: $[\alpha]_D$+22.7°, $[\alpha]_{546}$+27.2° (c 12 gL$^{-1}$, ethyl acetate); $^1$H NMR (CDCl$_3$) δ7.48–7.26 (m, 15H), 721–710 (M, 7H), 7.08–7.03 (m, 2H), 6.96–6.90 (m, 2H), 6.81, 6.78 (ABq, 2H, J=8.5 Hz, B part br), 6.32 (d, 1H, J=2 Hz), 6.29–6.24 (m, 2H), 6.05 (d, 1H, J=2.5 Hz), 5.15 (s, 2H), 5.05 (s, 2H), 5.04–4.80 (m, 6H), 4.54 (d, 1H, J=12.5 Hz), 4.23 (s, 1H), 3.83 (s, 3H), 3.77 (s, 3H), 3.21 (s, 3H); $^{13}$C NMR (CDCl$_3$) δ160.27, 160.04, 159.28, 158.63, 158.44, 154.61, 148.65, 147.95, 138.78, 137.46, 137.40, 137.03, 136.88, 132.67, 128.47, 128.35, 128.28, 128.17, 128.08, 127.83, 127.77, 127.63, 127.53, 127.39, 127.29, 127.24, 126.99, 126.72, 119.51, 114.96, 114.61, 113.74, 111.39, 94.62, 94.27, 93.47, 92.20, 79.90, 76.13, 74.69, 74.52, 71.30, 70.95, 69.96, 69.86, 56.60, 56.00, 55.20; IR (film) 3535, 1605, 1590, 1151, 1117, 736, 697 cm$^{-1}$. Anal. Calcd. for C$_{59}$H$_{54}$O$_{10}$: C, 76.77; H, 5.90. Found: C, 76.43; H, 5.48.

Example 5

Preparation of 3,5,7,3',4'-penta-O-benzyl-4α-(2,4,6-trimethoxyphenyl)epicatechin.

(a) Reduction with triethylsilane/trifluoroacetic acid: To a solution of 22 mg (24 µmol) of 3,5,7,3',4'-penta-O-benzyl-4-hydroxy-4-(2,4,6-trimethoxyphenyl)epicatechin in 1 mL of dichloromethane was added at room temperature 38 µL (0.24 mmol) of triethylsilane and then 22 µL (0.29 mmol) of trifluoroacetic acid. After 2 hours, solid sodium carbonate was added. Filtration, evaporation, and purification by thin layer chromatography (ethyl acetate/hexane 1:3) gave 15 mg (69%) of the product.

(b) Reduction with tributyltin hydride/trifluoroacetic acid: To a solution of 46 mg (24 µmol) of 3,5,7,3',4'-penta-O-benzyl-4-hydroxy-4-(2,4,6-trimethoxyphenyl)-epicatechin in 1 mL of dichloromethane was added at room temperature 20 µL (74 µmol) of tributyltin hydride and then 75 µL of 1 M trifluoroacetic acid/dichloromethane. After 10 min, solid sodium carbonate was added. Filtration, evaporation, and purification by thin layer chromatography (ethyl acetate/hexane 1:2) gave 39 mg (86%) of the product: $[\alpha]_D$−29.0°, $[\alpha]_{546}$43.7° (c 12 gL$^{-1}$, ethyl acetate); $^1$H NMR (CDCl$_3$) δ7.48–7.25 (m, 16H), 7.21–7.14 (m, 3H), 7.06–6.97 (m, 4H), 6.90 (d, 1H, J=8 Hz), 6.79–6.74 (m, 2H), 6.66–6.61 (m, 2H), 6.33 (d, 1H, J=2.5 Hz), 6.20 (d, 1H, J=2 Hz), 6.11 (d, 1H, J=2.5 Hz), 6.03 (d, 1H, J=2 Hz), 5.16 (s, 2H), 5.05–4.97 (m, 3H), 4.94–4.88 (m, 3H), 4.77, 4.68 (ABq, 2H, J=11.5 Hz), 3.94 (d, 1H, J=6.5 Hz), 3.78 (s, 3H), 3.69 (s, 3H), 3.58, 3.49 (ABq, 2H, J=11 Hz), 3.26 (s, 3H); $^{13}$C NMR (CDCl$_3$) δ161.04, 159.26, 158.17, 158.14, 157.44, 156.54, 148.97, 148.15, 138.04, 137.43, 137.39, 137.17, 137.01, 132.82, 128.51, 128.49, 128.39, 128.31, 127.88, 127.82, 127.68, 127.61, 127.55, 127.51, 127.42, 127.31, 127.12, 126.88, 126.84, 119.72, 114.94, 113.72, 110.80, 108.07, 94.99, 93.30, 92.22, 90.82, 79.98, 74.95, 71.45, 71.02, 69.97, 69.52, 56.21, 55.97, 55.25, 35.11; IR (film) 1605, 1590, 1151, 1113, 736, 697 cm$^{-1}$. Anal. Calcd. for C$_{59}$H$_{54}$O$_9$: C, 78.12; H, 6.00. Found: C, 77.78; H, 5.89.

Example 6

Preparation of 3,5,7,3',4'-penta-O-acetyl-4α-(2,4,6-trimethoxyphenyl)epicatechin.

To a solution of 100 mg (110 µmol) of 3,5,7,3',4'-penta-O-benzyl-4α-(2,4,6-trimethoxyphenyl)epicatechin in 6 mL of methanol/ethyl acetate 2:1 was added 20 mg of 20% palladium hydroxide on carbon. The mixture was stirred under 1 bar of hydrogen for 3 hours, after which period thin layer chromatography indicated completion of the reaction. The catalyst was filtered off and washed with methanol. The solution was evaporated, and the residue was dried in vacuo and dissolved at room temperature in 4 mL of acetic anhydride/pyridine. After stirring overnight, the mixture was evaporated, 40 mL of dichloromethane was added, the phases were separated, and the organic phase was washed five times with 10 mL of water and 10 mL of brine and dried over magnesium sulfate. The solution was evaporated, and the crude product was purified by thin layer chromatography (ethyl acetate/hexane 1:1) to give 30 mg (41%) of the pentaacetate: $[\alpha]_D$−38.8°, $[\alpha]_{546}$−48.0° (c 12 gL$^{-1}$, ethyl acetate); $^1$H NMR (CDCl$_3$) δ7.44 (d, 1H, J=2 Hz), 7.33, 7.18 (ABq, 2H, J=8.5 Hz, A part d with J=2 Hz), 6.73, 6.44 (ABq, 2H, J=2.5 Hz), 6.11, 5.98 (ABq, 2H, J=2.5 Hz), 5.68 (d, 1H, J=5.5 Hz), 5.25 (s, 1H), 5.00 (d, 1H, J=5.5 Hz), 3.88 (s, 3H), 3.77 (s, 3H), 3.36 (s, 3H), 2.27 (s, 9H), 1.58 (s, 6H); $^{13}$C NMR (CDCl$_3$) δ169.57, 169.02, 168.07, 168.05, 167.74, 160.34, 160.00, 158.55, 155.37, 148.98, 148.46, 141.87, 141.54, 136.10, 124.18, 123.04, 121.77, 115.91, 108.74, 108.15, 105.86, 90.83, 90.17, 77.63, 68.46, 56.11, 55.38, 55.16, 33.78, 21.11, 20.63, 20.06, 19.77; IR (film) 1766, 1741, 1589, 1369, 1202, 1114 cm$^{-1}$. Anal. Calcd. for C$_{34}$H$_{34}$O$_{14}$: C, 61.26; H, 5.14. Found: C, 61.08; H, 5.02.

Example 7

Preparation of 5,7,3',4'-tetra-O-benzyl-3-O-(tert-butyldimethylsilyl)epicatechin.

A solution of 4.37 g (6.72 mmol) of 5,7,3',4'-tetra-O-benzylepicatechin (Tückmantel et al. *J. Am. Chem. Soc.* 1999, 121, 12073–12081), 0.69 g (10.1 mmol, 1.5 eq.) of imidazole, and 1.42 g (9.4 mmol, 1.4 eq.) of tert-butyldimethylsilyl chloride in 6 mL of anhydrous N,N-dimethylformamide was stirred at room temperature in a closed flask for 19.5 hours. Direct column chromatography on silica gel with ethyl acetate/hexane 1:5, followed by evaporation and drying in vacuo gave 5.02 g (98%) of the silyl ether as a yellowish glass: $^1$H NMR δ7.47–7.25 (m, 20H), 7.11 (s, 1H), 6.94, 6.90(ABq, 2H, J=1 Hz), 6.24 6.22 (ABq, 2H, J=2 Hz)5.15 (s, 2H), 5.14 (narrow ABq, 2H), 5.03 (s, 2H), 5.02, 4.98 (ABq, 2H, J=11.5 Hz), 4.93 (s, 1H), 4.18 (narrow m, 1H), 2.86, 2.77 (ABq, 2 H, J=17 Hz, both parts d with J=4 Hz), 0.76 (s, 9H), −0.15 (s, 3H), −0.30 (s, 3H): $^{13}$C NMR (CDCl$_3$, TMS) δ158.49, 157.85, 155.56, 148.69, 148.29, 137.39, 137.36, 137.25, 137.01, 132.75, 128.55, 128.49, 128.41, 127.93, 127.74, 127.69, 127.63, 127.47, 127.31, 127.07, 120.07, 115.03, 114.21, 101.66, 94.49, 93.45, 78.93, 71.47, 71.36, 70.08, 69.88, 67.48, 28.38, 25.78, 18.07, −5.09, −5.12, −IR (film) 1619, 1592, 1499, 1259, 1146, 1120, 735, 696 cm$^{-1}$. Anal. Calcd. for C$_{49}$H$_{52}$O$_6$Si: C, 76.93; H, 6.85. Found: C, 77.17; H, 6.62.

Example 8

Preparation of 5,7,3',4'-tetra-O-benzyl-3-O-(tert-butyldimethylsilyl)-4-hydroxyepicatechin.

To a solution of 1.52 g (1.98 mmol) of 5,7,3',4'-tetra-O-benzyl-3-O-(tert-butyldimethylsilyl)epicatechin in 10 mL of tetrahydrofuran and 0.10 mL (5.6 mmol) of water was added at room temperature 1.34 g (5.9 mmol) of 2,3-dichloro-5,6-dicyano-p-benzoquinone. The mixture was stirred overnight, then 0.61 g (5.0 mmol) of 4-(dimethylamino)pyridine was added, stirring was continued for 5 min, and 20 g of silica gel was added. After evaporation, the residue was filtered over silica gel (ethyl acetate/hexane 1:4) to give 1.12 g (72%) of the product as a white foam: $[\alpha]_D$+2.0°, $[\alpha]_{546}$+2.2° (c 10 gL$^{-1}$, ethyl acetate); $^1$H NMR (CDCl$_3$) δ7.49–7.22 (m, 20H), 7.14 (d, 1H, J=2 Hz), 7.02, 6.95 (ABq, 2H, J=8.5 Hz, A part d with J=1.5 Hz), 6.27, 6.25 (ABq, 2H, J=2.5 Hz), 5.17 (s, 4H), 5.11 (narrow ABq, 2H), 5.02 (s, 2H), 5.00 (s, 1H), 4.79 (d, 1H, J=2 Hz), 3.88 (dd, 1H, J=1, 2.5 Hz), 2.35 (s, 1H), 0.70 (s, 9H), −0.21 (s, 3H), −0.45 (s, 3H). $^{13}$C NMR (CDCl$_3$) δ160.11, 158.86, 156.27, 148.87, 148.26, 137.32, 137.28, 136.67, 132.20, 128.64, 128.57, 128.41, 128.38, 128.02, 127.99, 127.74, 127.66, 127.62, 127.46, 127.29, 127.09, 120.09, 115.25, 113.98, 104.63, 94.51, 93.67, 75.37, 71.66, 71.47, 71.28, 70.03, 64.18, 25.67, 17.98, −5.37, −5.51; IR (film) 1617, 1593, 1259, 1153, 1026, 835, 736, 697 cm$^{-1}$. Anal. Calcd. for C$_{49}$H$_{52}$O$_7$Si : C, 75.35; H, 6.71. Found: C, 75.21; H, 6.65.

Example 9

Preparation of (2R, 3S)-5,7,3',4'-tetra-O-benzyl-3-α-(tert-butyl-dimethylsilyl)oxy]flavan-4-one To a solution of 0.39 g (0.50 mmol) of 5,7,3',4'-tetra-O-benzyl-3-O-(tert-butyldimethylsilyl)-4-hydroxyepicatechin in 2 mL of dry dichloromethane was added at room temperature 100 mg of 4 Å molecular sieves, 60 mg (0.55 mmol) of N-methylmorpholine-N-oxide, and 20 mg (55 μmol) of tetra-propylammonium perruthenate. The reaction mixture was stirred overnight and evaporated, and the residue was purified by column chromatography (ethyl acetate/hexane 1:4) to give 0.38 g (99%) of the ketone as a white foam: $[\alpha]_D$−32.5°, $[\alpha]_{546}$−39.2° (c 12 gL$^{-1}$, ethyl acetate); $^1$H NMR (CDCl$_3$) δ7.52–7.26 (m, 20H), 7.12 (br s, 1H), 7.00, 6.94 (ABq, 2H, J=8.5 Hz, A part d with J=1 Hz), 6.22, 6.18 (ABq, 2H, J=2 Hz), 5.25 (s, 1H), 5.22–5.12 (m, 6H), 5.05, 5.01 (ABq, 2H, J=11.5 Hz), 4.01 (d, 1H, J=1.5 Hz), 0.72 (s, 9H), −0.11 (s, 3H), −0.25 (s, 3H); $^{13}$C NMR (CDCl$_3$) δ188.67, 164.60, 163.94, 161.18, 148.78, 148.73, 137.14, 136.53, 135.77, 129.59, 128.64, 128.46, 128.43, 128.40, 128.29, 127.78, 127.71, 127.62, 127.50, 127.38, 127.22, 126.41, 120.12, 114.90, 113.98, 104.51, 95.04, 94.32, 81.48, 75.10, 71.31, 71.28, 70.19, 70.14, 25.61, 18.12, −5.08, −5.37; IR (film) 1680, 1608, 1268, 1164, 1121, 736, 696 cm$^{-1}$. Anal. Calcd. for C$_{49}$H$_{50}$O$_7$Si: C, 75.55; H, 6.47. Found: C, 75.67; H, 6.39.

Example 10

Preparation of 5,7,3',4'-tetra-O-benzyl-8-bromo-3-O-(tert-butyldimethylsilyl)epicatechin.

A solution of 180 mg (247 μmol) of 5,7,3',4'-tetra-O-benzyl-8-bromoepicatechin (Tückmantel et al. *J. Am. Chem. Soc.* 1999, 121, 12073–12081), 56 mg (0.37 mmol) of tert-butyldimethylsilyl chloride, and 49 mg (0.72 mmol) of imidazole in 1 mL of anhydrous N,N-dimethylformamide was stirred at room temperature overnight. The mixture was poured into ice water and extracted three times with 20 mL of ether. The combined organic phases were washed three times with 20 mL of water and 20 mL of brine and dried over magnesium sulfate. Evaporation and column chromatography (silica gel, dichloromethane/ethyl acetate/hexane 1:1:4) gave 187 mg (88%) of product as a foam: $^1$H NMR (CDCl$_3$) δ7.49–7.27 (m, 20H), 7.19 (d, 1H, J=1.5 Hz), 6.95, 6.89 (ABq, 1H, J=8.5 Hz, A part d with J=1.5 Hz), 6.20 (s, 1H), 5.15 (s, 4H), 5.08 (s, 3H), 4.99 (s, 2H), 4.22 (m, 1H), 2.89–2.73 (m, 2H), 0.72 (s, 9H), −0.16 (s, 3H), −0.33 (s, 3H); $^{13}$C NMR (CDCl$_3$) δ156.28, 154.40, 151.82, 148.60, 148.02, 137.37, 137.25, 136.81, 136.72, 132.19, 128.51, 128.48, 128.37, 128.35, 127.87, 127.79, 127.64, 127.61, 127.35, 127.22, 127.02, 127.00, 119.44, 114.96, 113.62, 103.48, 92.46, 79.18, 71.38, 71.13, 70.96, 70.16, 28.36, 25.63, −5.22, −5.26.

Example 11

Preparation of 5,7,3',4'-tetra-O-benzyl-3-O-(tert-butyldimethylsilyl)-4-hydroxyepicatechin-4,8-[5,7,3',4'-tetra-O-benzyl-3-O-(tert-butyldimethylsilyl)epicatechin.

To a solution of 450 mg (533 μmol) of 5,7,3',4'-tetra-O-benzyl-8-bromo-3-O-(tert-butyldimethylsilyl)epicatechin in 2 mL of dry tetrahydrofuran was added under nitrogen atmosphere at −78° C. 0.64 mL (1.1 mmol) of tert-butyllithium (1.7 M in pentane). After stirring at −78° C. for 60 min, a solution of 280 mg (359 μmol) of (2R,3S)-5,7,3',4'-tetra-O-benzyl-3-O-[(tert-butyldimethylsilyl)oxy]flavan-4-one in 2 mL of dry tetrahydrofuran was added. After another 3 hours at −78° C., 2 mL of aqueous ammonium chloride was added, and the mixture was allowed to warm to room temperature and extracted three times with 20 mL of dichloromethane. The combined organic phases were dried over magnesium sulfate and evaporated, and the residue was chromatographed on silica gel (dichloromethane/ethyl acetate/hexane 1:1:10) to give 410 mg (74%) of the product as a colorless foam: $[\alpha]_D$−9.2°, $[\alpha]_{546}$−11.6° (c 24 gL$^{-1}$, ethyl acetate); $^1$H NMR (CDCl$_3$) δ7.45–7.10 (m, 37H), 7.07 (t, 2H, J=7.5 Hz), 6.95–6.84 (m, 4H), 6.79 (t, 2H, J=8 Hz), 6.48 (d, 1H, J=8 Hz), 6.14 (s, 1H), 5.95 (d, 1H, J=2 Hz), 5.65 (d, 1H, J=2 Hz), 5.43 (d, 1H, J=2.5 Hz), 5.32 (d, 1H, J=11.5 Hz), 5.12° approx. 4.8 (m, 9H), 4.93, 4.85 (ABq, 2H, J=12 Hz), 4.80–4.70 (m, 3H), 4.63, 4.41 (ABq, 2H, J=11 Hz), 4.61 (d, 1H, J=11.5 Hz), 4.09 (s, 1H), 3.84 (br s, 1H), 2.88, 2.79 (ABq, 2H, J=17 Hz, B part d with J=4 Hz), 0.78 (s, 9H), 0.70 (s, 9H), −0.25 (s, 3H), −0.27 (s, 3H), −0.33 (s, 3H), −0.46 (s, 3H); $^{13}$C NMR (CDCl$_3$) δ158.46, 157.95, 157.32, 155.93, 154.14, 153.06, 148.42, 148.37, 147.71, 147.62, 137.72, 137.63, 137.61, 137.51, 137.35, 137.26, 137.21, 137.18, 133.41, 132.68, 128.56, 128.47, 128.33, 128.30, 128.28, 128.26, 128.21, 127.95, 127.64, 127.60, 127.51, 127.43, 127.26, 127.20, 127.12, 126.95, 119.99, 118.89, 115.46, 114.65, 114.54, 114.43, 113.63, 111.74, 103.42, 94.96, 94.31, 93.71, 79.37, 76.14, 75.40, 73.89, 72.79, 71.47, 71.31, 71.23, 70.15, 69.88, 69.62, 66.88, 29.90, 26.12, 25.76, 18.12, 16.98, −4.90, −5.03, −5.32, −5.40; IR (film) 1591, 1511, 1266, 1119, 1026, 835, 735, 696 cm$^{-1}$.

Example 12

Preparation of 5,7,3',4'-tetra-O-benzyl-3-O-(tert-butyldimethylsilyl)-epicatechin-4α,8-[5,7,3',4'-tetra-O-benzyl-3-O-(tert-butyldimethylsilyl)-epicatechin].

To a solution of 240 mg (155 μmol) of 5,7,3',4'-tetra-O-benzyl-3-O-(tert-butyldimethylsilyl)-4-hydrox-epicatechin-4,8-[5,7,3',4'-tetra-O-benzyl-3-O-(tert-butyldimethylsilyl)-epicatechin in 1 mL of dry dichloromethane was added at 0° C. 50 μL (186 μmol) of tri-n-butyltin hydride followed by 154 μL of trifluoroacetic acid (1 M in dichlormethane). After 1 hour, 1 g of solid sodium carbonate was added, and the solution was filtered and evaporated. The residue was chromatographed on silica gel (dichloromethane/ethyl acetate/hexane 1:1:10) to give 181 mg (76%) of the product as a colorless foam: $[\alpha]_D$−14.9°, $[\alpha]_{546}$−19.1° (c 15 gL$^{-1}$, ethyl acetate); $^1$H NMR (CDCl$_3$) δ7.49 (t, 4H, J=7 Hz), 7.44–7.15 (m, 34H), 7.13 (s, 1H), 7.09 (d, 1H, J=8.5 Hz), 6.97, 6.93 (ABq, 2H, J=8 Hz, B part br), 6.82, 6.61 (ABq, 2H, J=8 Hz, A part br), 6.77 (d, 2H, J=6.5 Hz), 6.08 (s, 1H), 6.05, 5.93 (ABq, 2H, J=2 Hz), 5.22–5.00 (m, 12H), 4.89 (s, 1H), 4.80 (d, 1H, J=11.5 Hz), 4.74, 4.68 (ABq, 2H, J=11 Hz), 4.59, 4.48 (ABq, 2H, J=11 Hz), 4.43 (d, 1H, J=5.5 Hz), 4.34 (d, 1H, partly overlapping), 4.31 (s, 1H), 4.02 (br d, 1H, J=2 Hz), 2.97, 2.85 (ABq, 2H, J=17 Hz, B part d with J=4.5 Hz), 0.71 (s, 9H), 0.61 (s, 9H), −0.32, −0.39, −0.89, −0.99 (each s, 3H); $^{13}$C NMR (CDCl$_3$) δ157.92, 157.34, 157.25, 155.52, 153.63, 148.97, 148.95, 148.40, 147.99, 137.67, 137.47, 137.43, 137.39, 137.26, 137.24, 137.19, 137.14, 133.84, 133.46, 128.51, 128.45, 128.39, 128.34, 127.89, 127.79, 127.73, 127.66, 127.62, 127.59, 127.55, 127.46, 127.35, 127.33, 127.08, 127.03, 126.65, 126.55, 119.87, 119.72, 115.29, 115.15, 114.47, 114.32, 110.32, 108.59, 101.60, 94.91, 93.18, 91.38, 81.25, 78.79, 71.67, 71.61, 71.40, 71.35, 71.28, 69.90, 69.70, 69.46, 69.15, 67.56, 36.90, 29.57, 26.09, 25.81, 18.16, 17.96, −5.21, −5.24, −5.42, −6.22. Anal. Calcd. for $C_{98}H_{102}O_{12}Si_2$: C, 77.03; H, 6.73. Found: C, 77.02; H, 6.63.

Example 13

Preparation of 5,7,3',4'-tetra-O-benzylepicatechin-4α,8-(5,7,3',4'-tetra-O-benzylepicatechin).

To a solution of 130 mg (85 μmol) of 5,7,3',4'-tetra-O-benzyl-3-O-(tert-butyldimethylsilyl)epicatechin-4α,8-(tert-butyldimethylsilyl) epicatechin] in 1 mL of acetonitrile was added at 0° C. 50 μL of 48% aq. hydrofluoric acid. The mixture was stirred at room temperature for 8 hours, then 10 mL of ethyl acetate was added, and the solution was washed with 10 mL each of aq. sodium bicarbonate, water, and brine. After drying over magnesium sulfate and evaporation, the residue was chromatographed on silica gel with dichloromethane/ethyl acetate/hexane 1:1:5 to give 89 mg (81%) of the product as a foam: $[\alpha]_D$ −94.2°, $[\alpha]_{546}$ −115° (c 9 gL$^{-1}$, ethyl acetate); $^1$H NMR (selection; 2 rotamers, approx. 3.2, MR=major, mr=minor rotamer) δ6.63 (d, 1H, MR, J=2 Hz), 6.35, 6.30 (ABq, 2H, MR, J=2 Hz), 6.05 (d, 1H, mr, J=1.5 Hz), 6.02 (s, 1H, MR), 4.25 (dd, 1H, MR, J=5.5, 9.5 Hz), 4.16 (dd, 1H, mr, J=5, 9 Hz), 3.60 (d, 1H, MR, J=9.5 Hz), 3.24 (d, 1H, mr, J=9 Hz), 2.99, 2.87 (ABq, 2H, mr, J=17.5 Hz, B part overlapping), 2.85, 2.69 (ABq, 2H, MR, J=17.5 Hz, B part d with J=5 Hz), 1.59 (d, 1H, MR, J=8 Hz), 1.39 (d, 1H, mr, J=5 Hz); $^{13}$C NMR (CDCl$_3$) δ159.03, 158.31, 158.14, 157.99, 157.02, 156.50, 156.29, 156.05, 155.94, 155.48, 153.38, 152.76, 149.1–148.4, 137.6–136.9, 136.55, 136.44, 132.07, 131.65, 130.51, 128.6–127.0, 120.49, 120.43, 119.42, 119.22, 115.0–114.2, 113.41, 113.30, 110.76, 110.29, 106.97, 106.30, 102.22, 101.40, 95.64, 95.03, 94.31, 93.98, 92.41, 91.98, 80.52, 79.84, 78.16, 77.88, 71.7–69.6, 66.07, 65.94, 35.89, 35.37, 28.84, 28.41. MS (API-ES, in methanol/NH$_4$OH) m/z 1316.6 (M+NH$_4^+$; calcd. for $^{13}C^{12}C_{85}H_{78}NO_{12}$ 1317.6), 1299.5 (M$^+$; calcd. for $^{13}C^{12}C_{85}H_{74}O_{12}$ 1299.5); 967.4; 649.3 (M$^{2+}$). Anal. Calcd. for $C_{86}H_{74}O_{12}$: C, 79.49; H, 5.74. Found: C, 79.59; H, 6.21.

Example 14

Preparation of 5,7,3',4'-tetra-O-benzylepicatechin-4α,8-[5,7,3',4'-tetra-O-benzyl-3-O-(3,4,5-tri-O-benzygalloyl)epicatechin].

To a suspension of 68 mg (154 μmol) of tri-O-benzylgallic acid and 1 μL of N,N-dimethylformamide in 1 mL of anhydrous dichloromethane was added 15 μL (0.17 mmol) of oxalyl chloride. After stirring at room temperature for 2 hours with exclusion of moisture, the resulting solution was evaporated and the residue dried in vacuo. A solution of 40 mg (31 μmol) of 5,7,3',4'-tetra-O-benzylepicatechin-4α,8-(5,7,3',4'-tetra-O-benzylepicatechin) in 0.5 mL of anhydrous pyridine was added to the crude acid chloride, 24 mg (0.20 mmol) of 4-(dimethylamino)pyridine was added, and the mixture was stirred at room temperature in a closed flask for 48 hours. After addition of 20 μL of water, stirring at room temperature was continued for 2 hours. Ten mL of 5% HCl was added, and the product was extracted into three times 5 mL of dichloromethane. The organic phases were dried over magnesium sulfate and concentrated, and the crude material was purified by column chromatography on silica gel with ethyl acetate/hexane 1:4. Evaporation and drying in vacuo yielded 50 mg (94%) of the product: $[\alpha]_D$ −122°, $[\alpha]_{546}$ −149° (ethyl acetate, c 12 gL$^{-1}$); $^1$H NMR (CDCl$_3$; selection; 2 rotamers, approx. 3:1, MR=major, mr=minor rotamer) δ6.54 (d, 1H, MR, J=8.5 Hz), 6.35 (d, 1H, mr, J=2 Hz), 6.08 (s, 1H, mr), 5.39 (narrow m, 1H, MR+mr), 5.18 (d, 1H, MR, J=5.5 Hz), 5.10 (d, 1H, MR, J=5 Hz), 4.30 (dd, 1H, MR, J=5.5, 9.5 Hz), 4.18 (s, 1H, MR), 4.12 (dd, 1H, mr, J=4.5, 9.5 Hz) 3.58 (d, 1H, MR, J=9.5 Hz), 3.18 (narrow m, 2H, mr), 3.10 (d, 1H, mr, J=9.5 Hz), 2.88 (narrow m, 2H, MR); $^{13}$C NMR (CDCl$_3$; weak signals of the minor rotamer omitted) δ165.10, 158.14, 158.00, 157.06, 156.47, 155.59, 153.00, 152.33, 148.67, 148.63, 148.44, 142.43, 137.5–136.4, 132.04, 131.31, 128.6–127.0, 124.92, 119.97, 119.55, 114.53, 114.36, 114.29, 113.26, 110.85, 108.74, 107.03, 101.98, 95.03, 94.01, 91.80, 80.69, 74.94, 71.14, 71.10, 70.99, 70.77, 69.94, 68.28, 35.53, 26.13. Anal. Calcd. for $C_{114}H_{96}O_{16}$: C, 79.51; H, 5.62. Found: C, 79.65; H, 5.38.

Example 15

Preparation of epicatechin-4α,8-(3-O-galloylepicatechin).

A solution of 22 mg (13 μmol) of 5,7,3',4'-tetra-O-benzylepicatechin-4α,8- [5,7,3',4'-tetra-O-benzyl-3-O-(3,4,5-tri-O-benzylgalloyl)epicatechin] in 4 of ethyl acetate/methanol (1:1) was hydrogenated at 3.5 bar and room temperature over 33 mg of 20% palladium hydroxide on carbon for 4.5 hours. After filtration over cotton and evaporation, the residue was lyophilized from 2 mL of water (HPLC grade) to give 6.3 mg (67%) of epicatechin-4α,8-(3-O-galloylepicatechin) as a colorless, amorphous solid: $^1$H NMR (CDCl$_3$; selection; 2 rotamers, approx. 3:1, MR=major, mr minor rotamer) δ7.06 (d, 1H, MR, J=1.5 Hz), 7.0–6.65 (m), 6.54 (d, 1H, mr, J=8.5 Hz), 6.47 (d, 1H, mr, J=2 Hz), 6.20 (d, 1H, mr, J=2 Hz), 6.15 (s, 1H, mr), 6.03 (dd, 1H, mr, J=2, 8.5 Hz), 5.99 (d, 1H, mr, J=2.5 Hz), 5.96 (d, 1H, MR, J=2 Hz), 5.93 (s, MR, 1H), 5.82 (d, 1H, MR, J=2 Hz), 5.56 (narrow m, 1H, MR+mr), 5.32 (narrow m, 1H, mr), 5.18 (s, 1H, MR), 5.08 (d, 1H, MR, J=5 Hz), 5.05 (d, 1H, mr, J=5 Hz), 4.28 (d, 1H, MR, J=5 Hz), 4.00 (d, 1H, mr, J=5 Hz), 3.07, 2.87 (ABq, 2H, MR, J=17.5 Hz, A part d with J=4.5 Hz), 2.96, 2.80 (ABq, 2H, mr, partially overlapping with the preceding signal). MS (electrospray) m/z 729.2 (M$^+$; calcd for $C_{37}H_{30}O_{16}$: 730.2).

Example 16

Preparation of 3,5,7,3',4'-penta-O-benzyl-8-bromoepicatechin.

To a suspension of 29 mg (0.73 mmol) of sodium hydride (60% in oil) in 2 mL of anhydrous N,N-dimethylformamide was added at room temperature 450 mg (617 μmol) of 5,7,3',4'-tetra-O-benzylepicatechin (Tückmantel et al. *J. Am. Chem. Soc.* 1999, 121, 12073–12081) in 3 mL of anhydrous N,N-dimethylformamide. After stirring for 30 min, 90 μL (0.73 mmol) of benzyl bromide and 20 mg (54 μmol) of tetrabutylammonium iodide were added. The mixture was stirred overnight, poured into ice water, and extracted three times with 50 mL of ethyl acetate. The combined organic phases were washed three times with 50 mL of water and 50 mL of brine, dried over magnesium sulfate, and evaporated.

Column chromatography (ethyl acetate/hexane 1:2) gave 480 mg (95%) of the product: $^1$H NMR (CDCl$_3$) δ7.50–7.15 (m, 23H), 6.99 (m, 2H), 6.95, 6.90 (ABq, 2H, J=8.5 Hz, A part d with J=1.5 Hz), 6.23 (s, 1H), 5.19 (s 2H), 5.11 (s, 4H), 4.97 (s, 2H), 4.38, 4.29 (ABq, 2H, J=12.5 Hz), 3.97 (narrow m, 1H), 2.95, 2.80 (ABq, 2H, J=17 Hz, both parts d with J=3.5 and 4.5 Hz, resp.); $^{13}$C NMR δ156.44, 154.62, 151.94, 148.65, 148.12, 137.92, 137.41, 137.26, 136.75, 136.71, 131.68, 119.15, 114.74, 113.29, 103.40, 93.11, 92.76, 78.06, 72.13, 71.32, 71.26, 71.21, 70.83, 70.22, 24.73; IR (film) 1605, 1580, 1177, 1125, 1095, 735, 697 cm$^{-1}$. Anal. Calcd. for C$_{50}$H$_{43}$BrO$_6$: C, 73.26; H, 5.29. Found: C, 72.81; H, 5.12.

Example 17

Preparation of 3,5,7,3',4'-penta-O-benzyl-8-bromocatechin.

To 0.23 g (5.8 mmol) of sodium hydride (60% suspension in mineral oil) was added with stirring at room temperature under nitrogen within 5 min 2.82 g (3.87 mmol) of 5,7,3', 4'-tetra-O-benzylcatechin (Tückmantel et al. *J. Am. Chem. Soc.* 1999, 121, 12073–12081 in 8 mL of anhydrous N,N-dimethylformamide. After 10 min, 0.74 mL (6.2 mmol) of neat benzyl bromide was added in 10 min with water cooling. The mixture was stirred at room temperature for 70 min, then cautiously hydrolyzed with 1 mL of water. 80 mL of water was added, the product was extracted into 40+20 mL of toluene, and the combined organic phases were washed with 80 mL of water and evaporated. The residue was chromatographed on silica gel; a forerun was removed with ethyl acetate/chloroform/hexane 1:2:17, and the product eluted with ethyl acetate/chloroform/hexane 1:9:10. Evaporation and drying in vacuo (room temperature, then 80° C.) yielded 3.13 g (99%) of the product as a colorless glass: [α]$_D$–15.7°, [α]$_{546}$–18.8° (ethyl acetate, c 41.2 gL$^{-1}$); $^1$H NMR (CDCl$_3$) δ7.48–7.21 (m, 23H), 7.10 (m, 2H), 7.00 (s, 1H), 6.91 (narrow ABq, 2H), 6.22 (s, 1H), 5.17 (s, 2H), 5.10 (narrow ABq, 4H), 4.99 (d, 1H, J=7 Hz), 4.97 (s, 2H), 4.34, 4.22 (ABq, 2H, J=12 Hz), 3.72 (dt, 1H, J=5.5 Hz (d), 7 Hz (t)), 2.88, 2.73 (ABq, 2H, J=17.5 Hz, both parts d with J=5.5 and 7.5 Hz, resp.); $^{13}$C NMR (CDCl$_3$) δ156.14, 154.66, 151.23, 148.69, 148.62, 137.87, 137.28, 137.12, 136.71, 136.65, 131.88, 128.59, 128.55, 128.46, 128.42, 128.27, 128.01, 127.89, 127.77, 127.71, 127.63, 127.36, 127.24, 127.17, 127.03, 119.80, 114.78, 113.37, 104.00, 92.72, 79.71, 74.03, 71.49, 71.29, 71.26, 70.99, 70.23, 25.32; IR (film) 1605, 1580, 1513, 1126, 1097, 736, 696 cm$^{-1}$.

Example 18

Preparation of 3,5,7,3',4'-penta-O-benzyl-4-hydroxyepicatechin-4,8-(penta-O-benzylepicatechin).

To a solution of 200 mg (244 μmol) of 3,5,7,3',4'-penta-O-benzyl-8-bromoepicatechin in 1 mL of dry tetrahydrofuran was added under nitrogen at –78° C. 0.30 mL (0.51 mmol) of tert-butyllithium (1.7 M in pentane). After stirring at –78° C. for 90 min, a solution of 120 mg (159 μmol) of (2R,3S)-3,5,7,3',4'-pentakis(benzyloxy)flavan-4-one in 1 mL of dry tetrahydrofuran was added. After another 3 hours at –78° C., 2 mL of aqueous ammonium chloride was added, and the mixture was allowed to warm to room temperature and extracted three times with 20 mL of dichloromethane. The combined organic phases were dried over magnesium sulfate and evaporated, and the residue was chromatographed on silica gel (dichloromethane/ethyl acetate/hexane 1:1:8) to give 165 mg (69%) of the product as a colorless foam: [α]$_D$–14.7°, [α]$_{546}$ –18.7° (c 10 gL$^{-1}$, ethyl acetate; $^1$H NMR (CDCl$_3$; 2 rotamers, ratio 1:5.5) major rotamer (or overlapping multiplets of both rotamers) δ7.47–6.84 (m, 52H), 6.79–6.70 (m, 4H), 6.44 (s, 1H), 6.37 (dd, 1H, J=8, 1 Hz), 5.95, 5.71 (ABq, 2H, J=2 Hz), 5.44 (s, 1H ), 5.12 (s, 1H), approx. 5.1–4.8 (m, 3H), 5.08 (s, 2H), 4.94 (s, 2H), 4.85 (s, 2H), 4.78, 4.73 (ABq, 2H, J=11.5 Hz), 4.61 (d, 1H, J=11.5 Hz), 4.61, 4.53 (ABq, 2H, J=11.5 Hz), 4.60 (d, 1H, J=12 Hz), 4.31 (d, 1H, J=12 Hz), 4.21 (s, 1H), 4.16 (s, 1H), 4.12 (d, 1H, J=12 Hz), 4.04 (d, 1H, J=12.5 Hz), 3.60 (d, 1H, J =2.5 Hz), 3.12, 2.68 (ABq, 2H, J=17.5 Hz, B part d with J=4.5 Hz), minor rotamer (discernible signals) δ5.14, 5.90 (2H, J=2 Hz), 6.09 (s, 1H), 3.90 (narrow m, 1H), 3.15, 2.91 (ABq, 2H, J=17.5 Hz, both parts d with J=2 and 4 Hz, resp.); $^{13}$C NMR (CDCl$_3$, major rotamer only) δ158.15, 157.86, 157.23, 156.96, 154.30, 154.07, 149.01, 148.1~, 148.10, 147.77, 138.90, 138.38, 137.59, 137.55, 137.47, 137.38, 137.35, 137.30, 137.08, 136.72, 133.07, 131.62, 128.62, 128.54, 128.39, 128.28, 128.24, 128.20, 128.14, 128.08, 128.00, 127.91, 127.76, 127.60, 127.48, 127.46, 127.22, 127.14, 127.07, 126.73, 126.99, 119.96, 119.80, 118.92, 114.74, 114.67, 113.67, 113.59, 113.44, 111.15, 102.28, 94.22, 93.84, 93.43, 81.34, 78.73, 76.30, 74.70, 74.56, 72.46, 72.19, 71.43, 71.01, 70.75, 69.91, 69.53, 69.38, 69.36, 25.56; IR (film) 3520 (br), 1592, 1511, 1267, 1118, 735, 696 cm$^{-1}$. Anal. Calcd. for C$_{100}$H$_{86}$O$_{13}$: C, 80.30; H, 5.80. Found: C, 80.20; H, 5.66.

Example 19

Preparation of penta-O-benzylepicatechin-4α,8-(penta-O-benzylepicatechin).

To a solution of 70 mg (46.8 μmol) of 3,5,7,3',4'-penta-O-benzyl-4-hydroxyepicatechin-4,8-(penta-O-benzylepicatechin) in 1 mL of dry dichloromethane was added at 0° C. 20 μL (74 μmol) of tri-n-butyltin hydride followed by 71 μL of trifluoroacetic acid (1 M in dichloromethane). After 1 hour, 1 g of solid sodium carbonate was added, and the solution was filtered and evaporated. The residue was chromatographed on silica gel (dichloromethane/ethyl acetate/hexane 1:1:8) to give 55 mg (79%) of the product as a colorless foam: [α]$_D$–48.7°, [α]$_{546}$ –59.6° (c 25 gL$^{-1}$, ethyl acetate); $^1$H NMR (CDCl$_3$; 2 rotamers, ratio 2.8:1; MR major, mr minor rotamer) δ7.48–6.74 (in, 56H), 6.62 (d, MR, 1H, J=8.5 Hz), 6.49 (br s, mr, 1H), 6.28–6.04 (m, 3H), 5.18–3.45 (series of m, 25H), 3.14, 2.77 (ABq, MR, 2H, J=17 Hz, both parts d with J=1 and 4 Hz, resp.), 2.93, 2.54 (ABq, mr, 2H, J=17.5 Hz, B part d with J=5 Hz); $^{13}$C NMR (CDCl$_3$; low intensity signals of minor rotamer omitted) δ158.04, 157.48, 156.79, 155.65, 152.93, 148.94, 148.76, 148.43, 148.10, 138.51, 138.34, 137.91, 137.47, 137.44, 137.39, 137.32, 137.24, 137.11, 132.98, 132.77, 128.57, 128.49, 128.47, 128.44, 128.38, 128.36, 128.28, 127.96, 127.75, 127.69, 127.61, 127.55, 127.50, 127.48, 127.38, 127.29, 127.27, 127.21, 127.17, 126.77, 119.77, 119.48, 114.51, 114.10, 113.83, 110.53, 108.29, 100.98, 94.96, 93.40, 92.31, 80.21, 78.13, 77.58, 75.06, 72.49, 71.39, 71.18, 71.11, 70.87, 70.70, 70.65, 70.03, 69.84, 69.60, 34.89, 24.89; IR (film) 1606, 1593, 1266, 1112, 734, 696 cm$^{-1}$. Anal. Calcd. for C$_{100}$H$_{86}$O$_{12}$: C, 81.17; H, 5.86. Found: C, 80.89; H, 5.62.

Example 20
Preparation of epicatechin-4α,8-epicatechin.

A solution of 40 mg (31 μmol) of 5,7,3',4'-tetra-O-benzylepicatechin-4α,8-(5,7,3',4'-tetra-O-benzylepicatechin) in 5 mL of methanol/tetrahydrofuran/water (20:20:1) was hydrogenated over 60 mg of 20% palladium hydroxide on carbon at room temperature and 5 bar for 5 hours. The catalyst was filtered off over celite, the solids were washed with 10 mL of methanol, and the solution was evaporated. The residue was taken up in HPLC grade water, and the solution was washed with 5 mL of toluene to remove nonpolar impurities. The solution was evaporated again and then lyophilized from 5 mL of HPLC grade water to give 13 mg (73%) of epicatechin-4α,8-epicatechin as a colorless, amorphous solid: $[\alpha]_D$ –38.6° (c 1.4 gL$^{-1}$, methanol); $^1$H NMR (CD$_3$OD, TMS; major rotamer only) δ7.06 (d, 1H, J=1 Hz), 7.01 (d, 1H, J=1 Hz), 6.90–6.68 (m, 4H), 5.99 (d, 1H, J=2 Hz), 5.92 (s, 1H), 5.83 (d, 1H, J=2 Hz), 5.04 (d, 1H, J=4.5 Hz), 4.96 (s, 1H), 4.94 (s, 1H), 4.30 (d, 1H, J=4.5 Hz), 4.29 (br, 1H), 2.95, 2.80 (ABq, 2H, J=17 Hz, both parts d with J=1.5 Hz, resp.); $^{13}$C NMR (CD$_3$OD, TMS; only signals listed which by their intensity appear to belong to the major rotamer) δ157.78, 156.82, 156.69, 154.48, 146.04, 145.94, 145.82, 145.76, 132.32, 132.30, 129.56, 128.92, 128.82, 119.21, 115.97, 115.89, 115.24, 100.74, 97.62, 97.49, 96.60, 80.98, 79.98, 72.33, 66.98, 36.71, 29.68; MS (electrospray) m/z 1155.6 ((2M)$^+$; calcd for C$_{60}$H$_{52}$O$_{24}$: 1156.3), 577.3 (M$^+$; calcd for C$_{30}$H$_{26}$O$_{12}$: 578.1). Anal. Calcd. for C$_{30}$H$_{26}$O$_{12}$·3.4H$_2$O: C, 56.32; H, 5.17. Found: C, 56.27; H, 4.82.

Example 21
Preparation of penta-O-acetylepicatechin-4α,8-(penta-O-acetylepicatechin).

To a solution of 75 mg (51 μmol) of penta-O-benzylepicatechin-4α,8-(penta-O-benzylepicatechin) in 2 mL of methanol and 1 mL of ethyl acetate was added 10 mg of 20% palladium hydroxide on carbon. The mixture was stirred under 1 bar of hydrogen for 10 hours, filtered, and evaporated. The crude deprotected dimer was dissolved in 3 mL of acetic anhydride/pyridine 1:2, and the mixture was stirred overnight. After evaporation, 30 mL of ethyl acetate was added. The solution was washed five times with 20 mL of water and 20 mL of brine, dried over magneisum sulfate, and evaporated. The residue was chromatographed on silica gel (ethyl acetate/hexane 2:1) to give 12 mg (24%) of the peracetate: $[\alpha]_D$+10.0°, $[\alpha]_{546}$+11.3° (c 6 gL$^{-1}$, ethyl acetate); $^1$H NMR (CDCl$_3$/benzene-d$_6$ 1:1) δ7.63 (s, 1H), 7.44 (s, 1H), 7.19 (s, 2H), 7.13 (s, 2H), 6.75, 6.64 (ABq, 2H, J=2 Hz), 6.62 (s, 1H), 6.57 (s, 2H), 5.85 (d, 1H, J=5.5 Hz), 5.24 (narrow m, 1H), 5.13 (d, 1H, J=5.5 Hz), 5.01 (s, 1H), 4.64 (s, 1H), 2.91, 2.69 (ABq, 2H, J=17. Hz, both parts d with J=2.5 and 3.5Hz, resp.), 2.023 (s, 3H), 2.018 (s, 3H), 1.97 (s, 3H), 1.96 (s, 3H), 1.94 (s, 3H), 1.92 (s, 3H), 1.82 (s, 3H), 1.74 (s, 3H), 1.70 (s, 3H), 1.63 (s, 3H); $^{13}$C NMR (CDCl$_3$/benzene-d$_6$ 1:1, TMS) δ170.47, 169.45, 168.68, 168.31, 168.04, 167.95, 167.78, 167.73, 167.67, 167.25, 155.79, 152.11, 149.99, 149.50, 148.92, 148.26, 142.69, 142.62, 142.20, 141.99, 136.18, 136.10, 125.00, 124.64, 123.34, 123.17, 122.01, 114.72, 114.26, 109.67, 109.60, 108.74, 108.51, 77.96, 77.83, 67.80, 65.80, 34.60, 25.70, 20.63, 20.44, 20.42, 20.32, 20.31, 20.27, 20.20, 19.96; IR (film) 1770, 1746, 1621, 1595, 1371, 1207, 903, 734 cm$^{-1}$.

What is claimed:

1. A protected dimer selected from the group consisting of 5,7,3',4'-tetra-O-benzyl-3-O-(tert-butyldimethylsilyl)epicatechin-4α,8-[5,7,3',4'-tetra-O-benzyl-3-O(tert-butyldimethylsilyl) epicatechin]; 3,5,7,3',4'-penta-O-benzylepicatechin-4α,8-(3,5,7,3',4'-penta-O-benzylepicatechin); and 5,7,3',4'-tetra-O-benzylepicatechin-4α,8-(5,7,3',4'-tetra-O-benzylepicatechin).

2. The dimer of claim 1 which is 5,7,3',4'-tetra-O-benzyl-3-O-(tert-butyldimethylsilyl)epicatechin-4α,8-[5,7,3',4'-tetra-O-benzyl-3-O(tert-butyldimethylsilyl) epicatechin].

3. The dimer of claim 1 which is 3,5,7,3',4'- penta-O-benzylepicatechin-4α,8-(3,5,7,3',4'-penta-O-benzylepicatechin).

4. The dimer is claim 1 which is 5,7,3',4'-tetra-O-benzylepicatechin-4α,8-(5,7,3',4'-tetra-O-benzylepicatechin).

5. A protected epicatechin-4α,8-epicatechin dimer having a 4-hydroxy group, which dimer is selected from the group consisting of 5,7,3',4'-tetra-O-benzyl-3-O-(tert-butyldimethylsilyl)- 4-hydroxyepicatechin-4α,8-[5,7,3',4'-tetra-O-benzyl-3-O-(tert-butyldimethylsilyl)epicatechin] and 3,5,7,3',4'-penta-O-benzyl-4 hydroxyepicatechin-4,8-(penta-O-benzylepicatechin).

6. The dimer of claim 5 which is 5,7,3',4'-tetra-O-benzyl-3-O-(tert-butyldimethylsilyl)-4-hydroxyepicatechin-4α,8-[5,7,3',4'-tetra-O-benzyl-3-O (tert-butyldimethylsilyl) epicatechin].

7. The dimer of claim 5 which is 3,5,7,3',4'-penta-O-benzyl-4 - hydroxyepicatechin-4α,8-(penta-O-benzylepicatechin).

8. A derivatized 5,7,3',4'-tetra-O-benzylepicatechin-4α,8-[5,7,3',4'-tetra-O-benzyl-epicatechin] dimer having at least one 3-O-acyl group.

9. The dimer of claim 8, wherein the 3-O-acyl group is introduced using an acid selected from the group consisting of caffeic acid, coumaric acid, ferulic acid, and sinapic acid as a derivatizing agent.

10. The dimer of claim 8, wherein the 3-O-acyl group is introduced using a hydroxy-protected acid selected from the group consisting of cinnamic acid, gallic acid, and hydroxybenzoic acid as a derivatizing agent.

11. The dimer of claim 10, wherein the 3-O-acyl group is a 3-O-(3,4,5-tri-O-benzylgalloyl) group.

12. The dimer of claim 8 which is epicatechin-4α,8-(3-O-acylepicatechin).

13. The dimer of claim 8 which is epicatechin-4α,8-(3-O-galloylepicatechin).

14. An epicatechin-4α,8-epicatechin dimer.

15. A derivatized epicatechin-4α,8-epicatechin dimer having acyl group(s) at the 5,7,3', and/or 4'-positions.

16. A derivatized epicatechin-4α,8-epicatechin dimer having acyl group(s) at the 3,5,7,3' and/or 4' positions.

17. The dimer of claim 16 which has acyl groups at the 3,5,7,3' and 4' positions of both mers.

18. The dimer of claim 17 which is penta-O-acetyl-epicatechin-4α,8-(penta-O-acetylepicatechin).

\* \* \* \* \*

UNITED STATES PATENT AND TRADEMARK OFFICE
CERTIFICATE OF CORRECTION

PATENT NO. : 6,720,432 B2
DATED : April 13, 2004
INVENTOR(S) : Kozikowski et al.

Page 1 of 1

It is certified that error appears in the above-identified patent and that said Letters Patent is hereby corrected as shown below:

Column 20,
Line 13, "3-O(tert-butyldimethylsilyl) epicatechin]." should read
-- 3-O-(tert-butyldimethylsilyl) epicatechin] --.
Line 14, "3,5,7,3',4'- penta-O-" should read -- 3,5,7,3',4'-penta-O --
Line 24, "butyldimethysilyl)- 4" should read -- butyldimethysilyl)-4 --.
Line 26, "-4 hydroxy" should read -- 4-hydroxy- --.
Line 29, "5,7,3', 4'-tetra-O-benzyl-3-O (*tert*-butyldimethylsilyl)" should read
-- 5,7,3',4'-tetra-O-benzyl-3-O-(*tert*-butyldimethylsilyl) --
Line 31, "benzyl-4 - hydroxyepicatechin-4α,8-(penta-O-" should read
-- benzyl-4-hydroxyepicatechin-4α,8-(penta-O- --

Signed and Sealed this

Thirty-first Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,720,432 B2  
DATED : April 13, 2004  
INVENTOR(S) : Alan P. Kozikowski et al.

It is certified that error appears in the above-identified patent and that said Letters Patent is hereby corrected as shown below:

Column 17,
Lines 53-54, "3,5,7,3', 4'-penta-O-benzyl-4-hydroxyepicatechin -4,8-(penta-O-benzylepicatechin)," should read -- 3,5,7,3',4'-penta-O-benzyl-4-hydroxyepicatechin-(4 alpha,8)-(3,5,7,3',4'-penta-O-benzylepicatechin). --.

Column 20,
Lines 25-26, "3,5,7,3'4'-penta-O-benzyl-4-hydroxyepicatechin-4,8-(penta-O-benzylepicatechin)," should read -- and 3,5,7,3',4'-penta-O-benzyl-4-hydroxyepicatechin-(4 alpha,8)-(3,5,7,3'.4'-penta-O-benzylepicaetchin). --.

Signed and Sealed this

Twenty-ninth Day of November, 2005

JON W. DUDAS
*Director of the United States Patent and Trademark Office*